United States Patent [19]

Hisanaga et al.

[11] Patent Number: 4,876,245
[45] Date of Patent: Oct. 24, 1989

[54] FLUORINE-CONTAINING MACROLIDE COMPOUNDS AND THEIR USE

[75] Inventors: Yorisato Hisanaga, Ibaraki; Kazuhiro Shimokawa, Settsu; Toshihiko Kawano, Ohtsu; Yasunori Suita, Matsubara; Tsuneo Yamashita, Settsu, all of Japan

[73] Assignee: Daikin Industries Ltd., Osaka, Japan

[21] Appl. No.: 136,125

[22] Filed: Dec. 21, 1987

[30] Foreign Application Priority Data

Dec. 22, 1986 [JP] Japan .................. 61-307132

[51] Int. Cl.$^4$ .................. A61K 31/70; C07H 17/08
[52] U.S. Cl. .......................... 514/29; 536/7.2
[58] Field of Search .................. 536/7.2; 514/29

[56] References Cited

U.S. PATENT DOCUMENTS 4,514,562  4/1985  Toscano .................. 536/7.2
4,673,736  6/1987  Toscano .................. 536/7.2

Primary Examiner—Johnnie R. Brown
Assistant Examiner—Elli Peselev
Attorney, Agent, or Firm—Birch, Stewart, Kolasch & Birch

[57] ABSTRACT

A fluorine-containing macrolide compound of the formula:

wherein
$R^1$ is hydroxy or —OR (wherein R is $C_1$–$C_5$ alkyl),
$R^2$ is hydrogen or hydroxy, or
$R^1$ and $R^2$ together form a cyclic residue of the formula:

(wherein R' and R'' are independently hydrogen or $C_1$–$C_5$ alkyl), when $R^4$ is hydrogen or $C_1$–$C_5$ alkyl, or
$R^3$ is when $R^4$ is —OCOCH$_2$Ph (wherein Ph is phenyl),
$R^5$ is hydrogen or $C_1$–$C_5$ alkyl, and
$R^6$ is hydrogen or methyl and an antimicrobial agent containing the fluorine-containing macrolide compound (I) as an effective component.

2 Claims, No Drawings

FLUORINE-CONTAINING MACROLIDE COMPOUNDS AND THEIR USE

FIELD OF THE INVENTION

The present invention relates to a novel fluorine-containing macrolide compound which is useful as an antimicrobial agent.

BACKGROUND OF THE INVENTION

Erythromycin A, which is one of the macrolide antibiotics having antimicrobial activity, is widely clinically used. However, it is difficult to increase the blood concentration of erythromycin A since it is easily decomposed by an acid in the stomach when it is orally administered, due to its chemical unstability under acidic conditions.

As a result of an investigation to improve the chemical stability of erythromycin A, a fluorine-containing compound, 8-fluoroerythromycin A, was developed (cf. Japanese Patent Kokai Publication No. 140779/1982).

SUMMARY OF THE INVENTION

From the viewpoint that, when an erythoromycin A derivative contains fluorine atom it would have a high chemical stability under acidic conditions, the present inventors have made a further search for improved derivatives and it have found that an erythromycin derivative having fluorine atoms in 8- and 9-positions have excellent chemical stability.

An object of the present invention is to provide a novel fluorine-containing macrolide compound which has antimicrobial activity against aerobic bacteria, anaerobic bacteria, and the like and has improved chemical stability.

DETAILED DESCRIPTION OF THE INVENTION

According to the present invention, there is provided a fluorine-containing macrolide compound of the formula:

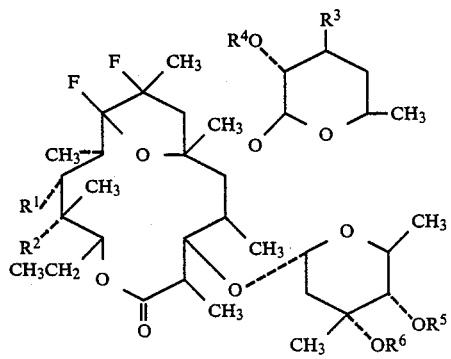

wherein
$R^1$ is hydroxy or —OR (wherein R is $C_1$-$C_5$ alkyl),
$R^2$ is hydrogen or hydroxy, or
$R^1$ and $R^2$ together form a cyclic residue of the formula:

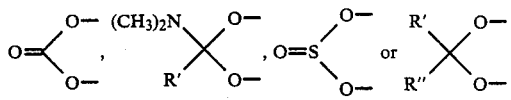

(wherein R' and R" are independently hydrogen or $C_1$-$C_5$ alkyl),
$R^3$ is

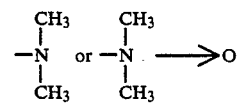

when $R^4$ is hydrogen or $C_1$-$C_5$ alkyl, or
$R^3$ is

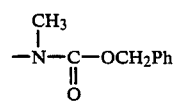

when $R^4$ is

(wherein Ph is phenyl),
$R^5$ is hydrogen or $C_1$-$C_5$ alkyl, and
$R^6$ is hydrogen or methyl and an antimicrobial agent containing the fluorine-containing macrolide compound (I) as the effective component.

The fluorine-containing macrolide compound of the present invention can be prepared for example by the following series of reactions (1) and (2) from a known erythromycin derivative which is comparatively easily obtainable:

(1) An erythromycin derivative of the following formula:

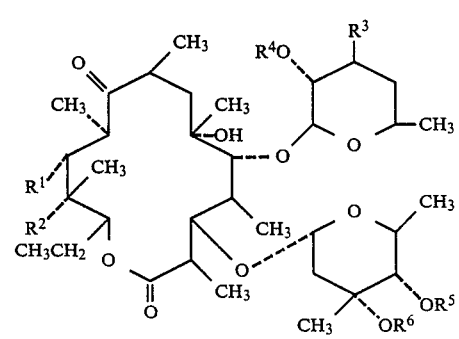

wherein $R^1$, $R^2$, $R^3$, $R^4$, $R^5$ and $R^6$ are the same as defined above is reacted with acetic acid to prepare a compound of the following formula:

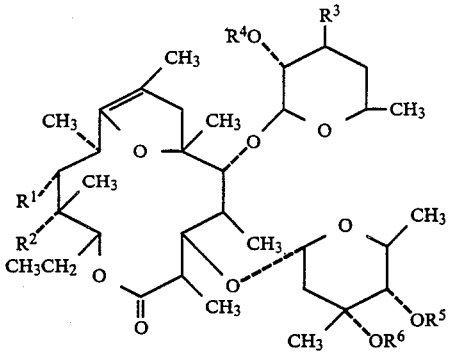

wherein $R^1$, $R^2$, $R^3$, $R^4$, $R^5$ and $R^6$ are the same as defined above.

(2) The compound obtained by the reaction (1) is reacted with fluorine ($F_2$) to give the compound of the present invention, which has the following formula:

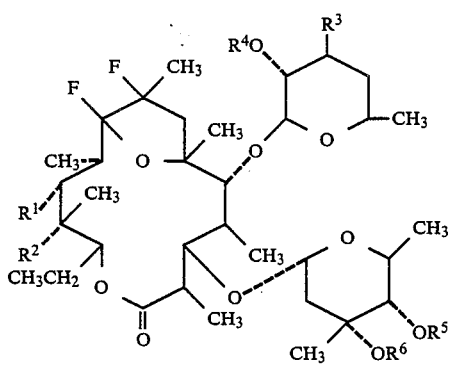

(I)

wherein $R^1$, $R^2$, $R^3$, $R^4$, $R^5$ and $R^6$ are the same as defined above.

The reaction (1) of an erythromycin derivative with acetic acid has been known and described for example in Experimentia, 27, (1971) 362.

In the above-mentioned fluorination reaction (2), although fluorine may be used as such, it is usually diluted with an inert gas such as nitrogen or helium. The concentration of fluorine is at least 1% by volume, preferably from 2 to 20% by volume. The reaction temperature in the fluorination is generally from −120° to +50° C., preferably from −80° to 0° C. The reaction is usually carried out in an inert solvent which is liquid at reaction temperature. Specific examples of the solvent are 1,1,2-trichloro-1,2,2-trifluoroethane, trichlorofluoromethane, dichloromethane, trichloromethane, tetrahydrofuran, dioxane, acetonitrile, formic acid, acetic acid, 2,2,3,3-tetrafluoropropanol and a mixture thereof.

Further, the present compound may be converted into a pharmaceutically acceptable derivative such as an ester, a salt-ester or a salt by esterification of the hydroxy in the 2'-position and/or neutralization of dimethylamino or N-oxide in the 3'-position according to known methods (cf. Japanese Patent Kokai Publication No. 140779/1982).

The fluorine-containing macrolide compound of the present invention may be blended with the usual additives such as excipients, vehicles and fillers and may be orally or intravenously administered in the form of a tablet, capsule, suspension, solution and the like (cf. Japanese Patent Kokai Publication No. 140779/82).

The fluorine-containing macrolide compound of the present invention has a higher chemical stability than erythromycin A under acidic conditions. In addition, the antimicrobial activity of the present compound against aerobic and anaerobic bacteria corresponds to that of erythromycin A.

The present invention will be hereinafter explained further in detail by following examples.

EXAMPLE 1

Preparation of 8,9-difluoroerythromycin A 6,9-epoxide

Glacial acetic acid (9.0 ml, 157 mmol) is added to erythromycin A (3.0 g, 4.1 mmol) and stirred for two hours at 25° C.

To the mixture, sodium acetate trihydrate (1.1 g, 8.1 mmol) is added and stirred for ten minutes. Then, chloroform (100 ml) is added and stirred until the mixture became homogeneous.

The obtained solution is cooled to −50° C. and then fluorine gas (6.7 mmol) diluted with nitrogen gas to 10% by volume is bubbled in the solution at a flow rate of 50 ml/min. with vigorously stirring.

Then, the temperature of the reaction mixture is raised to about 0° C. After adding sodium sulfite (100 mg) and calcium carbonate (2.0 g) and stirring, solid materials are filtered off.

After concentration of the filtrate, the residue is dissolved in methylene chloride (50 ml) and washed with saturated aqueous sodium bicarbonate solution. The organic phase is dried on magnesium sulfate and concentrated.

The concentrate was purified by means of a silica gel column with using a mixture of chloroform/methanol/triethylamine (volume ratio, 200/20/1) as an eluent and further purified by recrystallization from ethanol to give 8,9-difluoroerythromycin, 6,9-epoxide (884 mg). Yield 28.7%.

Melting point: 194.0° to 195.5° C.

Elemental analysis: Calculated: C 57.57%; H 8.75%; N 1.81%; F 4.92%. Found: C 57.80%; H 8.81%; N 1.83%; F 4.62%.

Mass spectra: 754 (M+N), 734 (M+H-HF), 596 (M+H-$C_5$ bound sugar) and 576 (M+H-$C_5$ bound sugar-HF)

$^1$H-NMR (solvent: $CDCl_3$): $\delta = 0.96$ (3H, t, —$C_2H_5$, J=7 Hz), 2.37 (6H, s, —N($CH_3$)$_2$) and 3.36 (3H, s, —$OCH_3$).

$^{19}$F-NMR (external standard: trifluoroacetic acid; solvent: $CDCl_3$): $\delta = 39.8$ (1F, dd, $F_9$, $J_{F8}=8$ Hz, $J_{H10}=27$ Hz) and 72.5 (1F, quint. d, $F_8$, $J_{F9}=8$ Hz, $J_{CH3,H7}=23$ Hz).

IR (cm$^{-1}$): 3450, 2980, 2920, 1730, 1455 and 1165.

EXAMPLE 2

Preparation of 8,9-difluoroerythromycin A 6,9-epoxide 11,12-carbonate

To a solution of 8,9-difluoroerythromycin 6,9-epoxide (200 mg, 0.27 mmol) in benzene (10.0 ml), anhydrous potassium carbonate (100 mg, 0.73 mmol) is added and the mixture is refluxed with stirring. Then, ethylene carbonate (180 mg, 2.18 mmol) dissolved in benzene (10.0 ml) was dropwise added to the mixture and refluxed for a day.

The completion of reaction is confirmed by means of silica gel thin layer chromatography with using a mixture of chloroform/methanol/triethylamine (volume ratio, 100/30/1) as a developer. Then, at room temperature, the reaction mixture is washed with water and dried on anhydrous sodium sulfate.

After concentration under a reduced pressure, the concentrate is purified by means of a silica gel column with using a mixture of chloroform/methanol/triethylamine (volume ratio, 200/20/1) as an eluent to give 8,9-difluoroerythromycin A 6,9-epoxide 11,12-carbonate (130 mg). Yield 63%.

IR (KBr, cm$^{-1}$): 3450, 2980, 1805 and 1740.

$^1$H-NMR (solvent: CDCl$_3$): δ=0.92 (3H, t, —C$_2$H$_5$, J=7.1 Hz), 2.32 (6H, s, —N(CH$_3$)$_2$) and 3.31 (3H, s, —OCH$_3$).

$^{19}$F-NMR (external standard: trifluoroacetic acid; solvent: CDCl$_3$): δ=44.0 (1F, dd, F$_9$, J$_{F8}$=12 Hz, J$_{H10}$=27 Hz) and 75.2 (1F, quint. d, F$_8$, J$_{F9}$=12 Hz, J$_{Me}$, H$_7$=20 Hz).

$^{13}$C-NMR (solvent: CDCl$_3$): δ=153.3 (carbonate carbonyl) and 177.2 (lactone carbonyl).

EXAMPLE 3

Preparation of 8,9-difluoroerythromycin A 6,9-epoxide 11,12-(N,N-dimethylacetamide) acetal To a solution of 8,9-difluoroerythromycin 6,9-epoxide (180 mg, 0.24 mmol) in benzene (3.0 ml), N,N-dimethylacetamide dimethylacetal (1.0 ml, 910 mg, 6.84 mmol) is added and the mixture is stirred for two days at room temperature in a nitrogen atmosphere.

After confirmation of disappearance of the spot of the starting substances by silica gel thin-layer chromatography with using a mixture of chloroform/methanol/triethylamine (volume ratio, 100/30/1) as a developer, the mixture is concentrated under a reduced pressure.

The residue is purified by means of a silica gel column with using a mixture of chloroform/triethylamine (volume ratio, 200/1) as an eluent to give 8,9-difluoroerythromycin A 6,9-epoxide 11,12-(N,N-dimethylacetamide) acetal (120 mg). Yield 65%.

IR (KBr, cm$^{-1}$): 3450, 2950 and 1735.

$^1$H-NMR (solvent: CDCl$_3$): δ=2.28 (s, 6H, N(CH$_3$)$_2$), 2.32 (s, 6H, N(CH$_3$)$_2$) and 3.34 (s, 3H, —OCH$_3$).

$^{19}$F-NMR (external standard: trifluoroacetic acid; solvent: CDCl$_3$): δ=44.4 (1F, dd, F$_9$, J$_{F8}$=14 Hz, J$_{H10}$=30 Hz) and 75.4 (1F, quint. d, F$_8$, J$_{F9}$=14 Hz, J$_{Me,H7}$=19 Hz).

EXAMPLE 4

Preparation of 8,9-difluoroerythromycin A 6,9-epoxide 11,12-sulfite

To a solution of 8,9-difluoroerythromycin 6,9-epoxide (400 mg, 0.54 mmol) in absolute methanol (6.0 ml), anhydrous potassium carbonate (500 mg, 3.65 mmol) is added and the mixture is stirred. Then, ethylene sulfate (1.0 ml, 1.46 g, 13.18 mmol) dissolved in absolute methanol (1.0 ml) is gradually added to the reaction suspension and stirred for three days.

After confirmation of completion of reaction by a silica gel thin-layer chromatography with using a mixture of chloroform/methanol/triethylamine (volume ratio, 100/30/1) as a developer, the reaction mixture is poured into water (10.0 ml) and extracted with ethyl acetate (12.0 ml) for three times. The combined organic phase is dried on anhydrous magnesium sulfate, concentrated under a reduced pressure and purified by means of a silica gel column with using a mixture of chloroform/triethylamine (volume ratio, 200/1) as an eluent to give 8,9-difluoroerythromycin A 6,9-epoxide 11,12-sulfite (200 mg). Yield 48%.

IR (KBr, cm$^{-1}$): 3370, 2950 and 1730.

$^1$H-NMR (solvent: CDCl$_3$): δ=0.91 (t, 3H, —C$_2$H$_5$, J=7.1 Hz), 2.47 (s, 6H, —N(CH$_3$)$_2$) and 3.29 (s, 3H, —OCH$_3$).

$^{19}$F-NMR (external standard: trifluoroacetic acid; solvent: CDCl$_3$): δ=44.4 (1F, dd, F$_9$, J$_{F8}$=13 Hz, J$_{H10}$=27 Hz) and 75.3 (1F, quint. d, F$_8$, J$_{F9}$=13 Hz, J$_{Me,H7}$=22 Hz).

EXAMPLE 5

Preparation of 8,9-difluoroerythromycin A 6,9-epoxide acetate

To a mixture of sodium bicarbonate (3760 g), acetone (30 ml) and 8,9-difluoroerythromycin A 6,9-epoxide (7.520 g, 10 mmol), anhydrous acetic acid (1.23 ml, 13 mmol) is added and the mixture is stirred for two hours at 25° C. and then poured into ice water. After two hours, the mixture is extracted three times with chloroform. The organic phase is washed with a saturated aqueous sodium bicarbonate solution and then water, and dried on anhydrous sodium sulfate. After evaporating off chloroform, the resulting solid is recrystallized from a mixture of ethyl ether and n-hexane to give 8,9-difluoroerythromycin A 6,9-epoxide acetate (6.325 g, 7.95 mmol).

IR (cm$^{-1}$): 3480, 1740, 1455, 1370, 1340, 1280, 1235, 1160, 1110, 1085, 1050, 1030, 1010, 995, 975 and 955.

EXAMPLE 6

Preparation of 8,9-difluoroerythromycin A 6,9-epoxide ethylsuccinate

In the same manner as in Example 5, but using ethylsuccinyl chloride in place of anhydrous acetic acid, 8,9-difluoroerythromycin A 6,9-epoxide ethylsuccinate is prepared.

IR (cm$^{-1}$): 3480, 1735, 1450, 1370, 1345, 1190, 1160, 1050, 1030, 1010, 995, 975, 955, 890 and 800.

EXAMPLE 7

Preparation of 8,9-difluoroerythromycin A 6,9-epoxide succinate

To a mixture of acetone (37.5 ml) and 8,9-difluoroerythromycin A 6,9-epoxide (7.520 g, 10 mmol), anhydrous succinic acid (1 g, 10 mmol) was added and the mixture is stirred for 15 minutes at 80° C. and then cooled to room temperature. After two hours, in the same manner as Example 5, the mixture is extracted, dried and recrystallized to give 8,9-difluoroerythromycin A 6,9-epoxide succinate (450 g, 7.55 mmol).

IR (cm$^{-1}$): 3450, 1730, 1575, 1455, 1370, 1340, 1190, 1160, 1050, 990, 975 and 950.

EXAMPLE 8

Preparation of 8,9-difluoroerythromycin A 6,9-epoxide stearate

To a mixture of acetone (20 ml) and 8,9-difluoroerythromycin A 6,9-epoxide (7.520 g, 10 mmol), a solution of stearic acid (2.85 g, 10 mmol ) in a mixture of acetone and distilled water (volume ratio, 1:1) is added. The solvents are evaporated off from the solution and the residue is recrystallized from a mixture of acetone and n-hexane to give 8,9-difluoroerythromycin A 6,9-epoxide stearate (10.2 g, 10.1 mmol).

IR (cm$^{-1}$): 3470, 1730, 1455, 1375, 1340, 1150, 1105, 1030, 1010, 990, 975, 950, 930, 890, 830 and 800.

EXAMPLE 9

The antimicrobial activities of 8,9-difluoroerythromycin 6,9-epoxide (Example 1), 8,9-difluoroerythromycin 6,9-epoxide 11,12-carbonate (Example 2) and 8,9-difluoroerythromycin 6,9-epoxide 11,12-sulfite (Example 4) are examined by an agar streak method and expressed in terms of minimal inhibitory concentrations (MIC, μg/ml) against the following bacteria. The results are shown in Tables 1 to 3.

TABLE 1

MIC against aerobic bacteria (gram-positive bacteria)

| bacteria | MIC Exam. 1 | Exam. 2 | Exam. 4 |
|---|---|---|---|
| *Streptococcus faecalis* | 1.25 | 0.625 | 0.625 |
| *Streptococcus pyogenes* | 0.011 | 0.011 | 0.011 |
| *Streptococcus pneumoniae* | 0.025 | 0.013 | 0.013 |
| *Bacillus natto* | 0.078 | 0.078 | 0.078 |
| *Staphylococcus aureus* | 0.156 | 0.156 | 0.156 |
| *Bacillus subtilis* | 0.049 | 0.049 | 0.049 |
| *Micrococcus luteus* | 0.006 | 0.02 | 0.02 |
| *Corynebacterium diphtheriae* | 0.011 | 0.022 | 0.022 |

TABLE 2

MIC against aerobic bacteria (gram-negative bacteria)

| bacteria | MIC Exam. 1 | Exam. 2 | Exam. 4 |
|---|---|---|---|
| *Escherichia coli* | 31.25 | 7.8 | 7.8 |
| *Hemophilus influenzae* | 3.5 | 7.0 | 7.0 |
| *Proteus vulgaris* | 26.0 | 26.0 | 26.0 |
| *Pseudomonas aeruginosa* | 26.0 | 26.0 | 26.0 |
| *Salmonella typhi* | 13.2 | 13.2 | 13.2 |
| *Shigella sonnei* | 25.0 | 12.5 | 12.5 |
| *Neisseria gonorrhoeae* | 0.052 | 0.052 | 0.052 |
| *Acholeplasma laidlawii* | 0.1 | 0.2 | 0.2 |
| *Mycoplasma homilis* | 25.0 | 25.0 | 25.0 |

TABLE 3

MIC against anaerobic bacteria

| bacteria | MIC Exam. 1 | Exam. 2 | Exam. 4 |
|---|---|---|---|
| *Bacterioides fragilis* | 0.21 | 0.84 | 0.84 |
| *Fusobacterium necrophorum* | 2.0 | 8.0 | 8.0 |
| *Clostridium perfringens* | 0.83 | 3.3 | 0.3 |

EXAMPLE 10

A certain amount of 8,9-difluoroerythromycin-6,9-epoxide or erythromycin A is dissolved in an aqueous solution (pH 2.97) or disodium citrate (0.1M) and hydrochloric acid (0.1M) (volume ratio, 4:6). Then, at certain intervals of time, the antimicrobial activities of the solutions are examined by a serial dilution method. The half-life period of the antimicrobial activity of 8,9-difluoroerythromycin 6,9-epoxide was three days and that of erythromycin A is ten minutes.

What is claimed is:

1. A fluorine-containing macrolide compound of the formula:

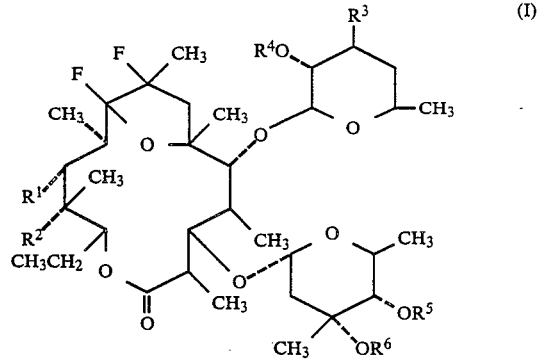

wherein
$R^1$ is hydroxy or —OR (wherein R is $C_1$-$C_5$ alkyl),
$R^2$ is hydrogen or hydroxy, or
$R^1$ and $R^2$ together form a cyclic residue of the formula:

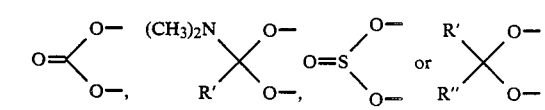

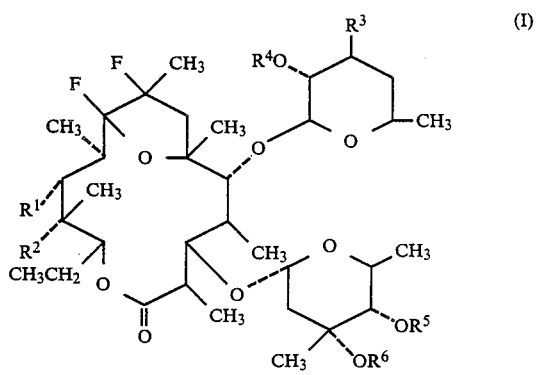

(wherein R' and R" are independently hydrogen or $C_1$-$C_5$ alkyl),
$R^3$ is

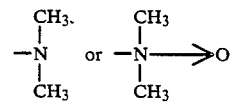

when $R^4$ is hydrogen or $C_1$-$C_5$ alkyl, or
$R^3$ is

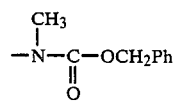

when $R^4$ is

(wherein Ph is phenyl), $R^5$ is hydrogen or $C_1$–$C_5$ alkyl, and $R^6$ is hydrogen or methyl.

2. An antimicrobial composition comprising, an effective amount of a fluorine-containing macrolide compound of the formula:

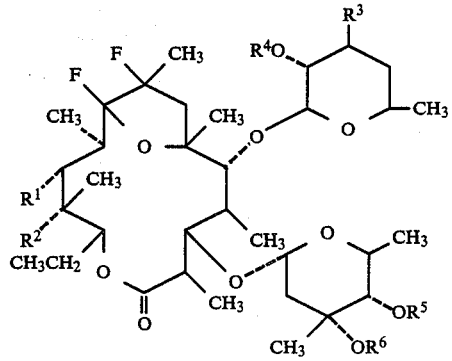
(I)

wherein $R^1$ is hydroxy or —OR (wherein R is $C_1$–$C_5$ alkyl), $R^2$ is hydrogen or hydroxy, or $R^1$ and $R^2$ together form a cyclic residue of the formula:

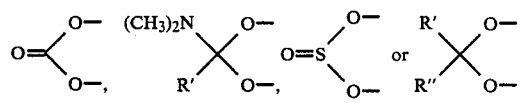

(wherein R' and R" are independently hydrogen or $C_1$–$C_5$ alkyl), $R^3$ is

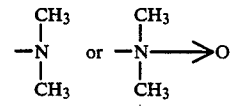

when $R^4$ is hydrogen or $C_1$–$C_5$ alkyl, or $R^3$ is $$-\underset{\underset{\text{CH}_3}{|}}{N}-\underset{\underset{O}{\|}}{C}-OCH_2Ph$$

when $R^4$ is

(wherein Ph is phenyl), $R^5$ is hydrogen or $C_1$–$C_5$ alkyl, and $R^6$ is hydrogen or methyl and a pharmaceutically acceptable carrier.

* * * * *